(12) United States Patent
Leaderman

(10) Patent No.: US 6,458,380 B1
(45) Date of Patent: Oct. 1, 2002

(54) DRESSING AND PREPARATION DELIVERY SYSTEM

(76) Inventor: Richard Leaderman, 1284 Elm St., West Springfield, MA (US) 01089

( * ) Notice: Subject to any disclaimer, the term of this patent is extended or adjusted under 35 U.S.C. 154(b) by 0 days.

(21) Appl. No.: 09/710,345

(22) Filed: Nov. 9, 2000

(51) Int. Cl.$^7$ .............................. A61F 13/00; A61K 9/70
(52) U.S. Cl. ...................... 424/443; 424/400; 424/401; 424/422; 424/423; 424/434; 424/435; 424/445; 424/484; 424/489; 424/49; 424/77
(58) Field of Search .................................. 424/400, 401, 424/422, 423, 434, 435, 443, 445, 484, 489, 49, 77

(56) References Cited

U.S. PATENT DOCUMENTS

| | | | | |
|---|---|---|---|---|
| 4,226,848 A | * | 10/1980 | Nagai et al. | 424/19 |
| 5,047,244 A | * | 9/1991 | Sanvordeket et al. | 424/435 |
| 5,578,315 A | * | 11/1996 | Chien et al. | 424/435 |
| 5,876,744 A | * | 3/1999 | Della Valle et al. | 424/434 |
| 5,891,558 A | * | 4/1999 | Bell et al. | 428/218 |
| 6,197,331 B1 | * | 6/2001 | Lerner et al. | 424/448 |

* cited by examiner

Primary Examiner—Thurman K. Page
Assistant Examiner—Charesse Evans
(74) Attorney, Agent, or Firm—Frommer Lawrence & Haug; Ronald R. Santucci

(57) ABSTRACT

A dressing and method of treating wounds is provided. The dressing can comprise water-soluble or swellable polymers which are capable of forming a viscous aqueous or non-aqueous solution and form a gel, particularly a foam form of the gel. The dressing can be constructed in the form of a sponge or sheet impregnated with the gel, or coated onto a non-porous, porous or micro-porous substrate. The dressing can also be provided in a form of a dehydrated powder, such as one which can be sprinkled under a flap of tissue and which will hold the flap down as a substitute for the use of stitches. Wounds treated with dressings in accordance with embodiment of the invention will tend to heal without the formation of a typical hard scab. The gel provides an excellent surface from which to apply tooth whitener to the teeth. The solubility of the material may be adjusted through the addition of non-interacting secondary raw materials to the liquid state formulation mix, or sprayed over the completed product to form a bi-layer, tri-layer, or other multiple layer material that can demonstrate varied solubility and degradation over time when compared to a single formulation mix and subsequent freeze drying or other means of processing to form the desired product.

30 Claims, No Drawings

DRESSING AND PREPARATION DELIVERY SYSTEM

BACKGROUND OF THE INVENTION

The invention relates to dressings and in particular, to dressings for wounds in the oral cavity and for delivering preparations, such as antibiotics, pain medication, or agents for whitening the teeth to selected parts of the body.

Conventional dressings for the oral cavity has not been fully satisfactory. The oral cavity has a high level of bacteria and thus, wounds, including ulcers cannot be adequately treated. Frequently, the wounds take several days to heal and if patients are to be sent home after the surgery, they need to eat during the healing time. This presents additional problems in constructing an appropriate dressing. Various methods of protecting the wound often result in slowed healing around what is commonly a plaster-like material used to cover the wound. This plaster-like dressing can become detached and there is then renewed possibility for infection and bleeding.

It is often necessary to deliver an antibiotic or other pharmaceutical, drug or preparation to a wound or to apply whitening agents to the teeth. However, when such preparations are applied within the oral cavity, it can be difficult to maintain the preparation in its proper location in view of the natural processes which occur within the mouth.

Accordingly, it is desirable to provide an improved wound dressing and system for applying drugs and other treatment preparations to wounds, which overcome the disadvantages of the prior art.

SUMMARY OF THE INVENTION

Generally speaking, in accordance with the invention, a dressing material and method of treating wounds and applying therapeutic materials and preparations to selected parts of the body is provided. The dressing can comprise a water-soluble polymer which is capable of forming a viscous aqueous or non-aqueous solution and form a gel. The gel can be dehydrated to form a foam or powder which can be reconstituted prior to use, or applied directly to a wound. The dressing can be constructed in the form of a sponge or sheet impregnated with the gel, or coated onto a non-porous, porous or micro-porous substrate. The dressing can also be provided in a form of a dehydrated powder, such as one which can be sprinkled under a flap of tissue and which will hold the flap down as a substitute for the use of stitches. Wounds treated with dressings in accordance with embodiments of the invention will tend to heal faster because there is less trauma to the wound or surgical site and because dressings in accordance with the invention do not interfere with healing the body, which can heal at a rapid rate.

Gels in accordance with the invention can comprise acrylic acid polymers, particularly acrylic acid polymers cross-linked with divinyl glycols, and in particular, pharmaceutical resin sold under the name NOVEON, by B.F. Goodrich, Chemical Co. and most preferably the acid form of polycarbophil, meeting the USP monograph for polycarbophil. The general structure of such a resin is the following: —[—CH$_2$—HCCOOH—]$_n$,— and is drawn below.

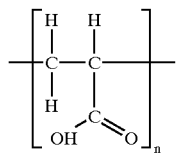

The gel can also be formed with preservatives, such as sorbic acid, hydroxides, such as sodium hydroxide and water. In use, the gel, gel in a carrier or gel, carrier and backing can adhere to gum surfaces and is easily removed by direct removal or washing.

Accordingly, it is an object of the invention to provide an improved wound dressing.

It is another object of the invention to provide an improved method of treating wounds.

Still another object of the invention is to provide an improved method and composition for treating wounds in the oral cavity.

DETAILED DESCRIPTION OF THE PREFERRED EMBODIMENTS

The invention provides a biodegradable matrix in the form of gel formulations and methods for producing the same, which also have the ability to contain, carry and apply chemical elements, such as antibiotics, anti-bacterial agents, bacterial-static agents and other drugs, for preventing or treating infection and to promote, enhance and speed the healing of wounds. The invention also comprises a carrier for the gel formulation, such as a gauze, sponge or other sheet that can become impregnated with the gel formulation and further processing by steps of severe dehydration, such as that associated with lyophilized processing to provide the gel formulation in powder form. The gel and/or gel/carrier composite can also be provided on a support.

The formulations and articles described herein are particularly useful for topical applications within the oral cavity. The formulations comprise water soluble, pharmaceutically and/or oral cavity compatible polymeric material for providing viscosity within acceptable ranges, as determined by the particular application of the gel. The gel formulation provides advantageous controlled release and increased contact time with the intended oral cavity site. Preparing and using therapeutic gels is discussed in U.S. Pat. Nos. 5,876,744 and 5,989,535, which themselves cite earlier patents on this issue and the contents of these patents are incorporated herein by reference.

Gel/carrier and gel/carrier/backing formulations of the present invention have the advantage of adhering to a gum or tooth surface and conforming to the irregular surface contours and membranes encountered within the oral cavity. The gel and composites comprising the gel with the carrier and/or backing may be applied directly to the gum or tooth surface or in conjunction with or without a compliant non-porous, porous or micro-porous substrate, for example, in the form of a coating, to be applied to the oral cavity site intended for specified activity. Composites in accordance with preferred embodiments of the invention have the further advantage of easy application to the oral cavity surface and easy removal by direct removal or washing. Embodiment of the invention can also exhibit the ability to permit increased activity to the intended site and further activity increase through moisture activation of components, if required.

Aqueous gels in accordance with preferred embodiments of the invention will have different viscosities depending on the intended application. The viscosity of gel material prior to the freeze dried processing can have significant effects for a number of reasons. A thinner low viscosity gel in the range of about 1,000 cps up to approximately 10,000 cps, will generally have a lower concentration of solids. The lower concentration of solids in solution can result in a thinner freeze dried product when compared to the same processing steps, lyophilization, applied to a thicker gel, with high viscosity in the range about 10,000 cps to 100,000+ cps, which generally have a higher concentration of solids in solution. Thus, adjusting the viscosity lends itself to the custom or tailored fabrication of the solid foam, porous sheet, resulting product. This would allow thicker materials to be utilized in extended time release of drug or preparation delivery products.

This would also allow thicker materials to fill larger void zones of the oral cavity intended for coverage. This would also lend the thicker product to potentially be less flexible and compliant to contours within the oral cavity where the wound dressing may be required. The thickness may benefit the product efficiency in the prevention of detritus permeation through the dressing to the covered site.

It should also be noted, that this product, regardless of initial thickness, after primary processing (freeze drying), may be pressed via a secondary process step after the completion of the freeze drying procedure. This additional step would allow the physical characteristics, and potential flexibility benefits of a thinner product to be experienced by a "thicker" freeze dried product, resulting in what may be considered a concentrated product formulation or processing step.

The solubility of the material may be adjusted through the addition of non-interacting secondary raw materials to the liquid state formulation mix, or sprayed over the completed product to form a bi-layer, tri-layer, or other multiple layer material that can demonstrate varied solubility and degradation over time when compared to a single formulation mix and subsequent freeze drying or other means of processing to form the desired product.

Gel forming materials in accordance with preferred embodiments of the invention can comprise water-soluble polymers capable of forming a viscous aqueous solution of a non-water soluble material. Water-swellable polymers, which can also form a viscous solution are also preferred. As used herein, the terms swellable polymers will refer to those polymers which absorb water rather than dissolve in water. Cross-linked forms of the polymers described herein may not be water soluble, but may be water swellable. As used herein, cross-linking encompasses, but is not limited to covalently bonding polymer chains with bifunctional reagents. It will also be understood by those of ordinary skill in the art that certain polymers may have to be used in the salt or acid form or a partially neutralized form in order to be made water-soluble or to obtain the viscosity characteristics devised by a specific application. Thus, unless otherwise specified, the identification of a polymer will also refer to the salt, acid or chelated form of the polymer. Preferred dressings will be able to adhere to a wound site, such as one within the oral cavity for at least 24 hours.

Preferred polymers for forming aqueous gel formulations in accordance with preferred embodiments of the invention include vinyl polymers, polyoxyethylene-polyoxypropylene copolymers, polysaccharides, proteins, poly(ethylene) oxides, acrylamide polymers and derivatives and salts thereof. It is also to be understood that poly(ethylene)oxides includes polyethylene glycol. For applications in which ingestion of the formulation may occur, it is preferred not to employ polyoxyethylene polyoxypropalene copolymers or poly(ethyleneoxide).

Vinyl polymers, also known as substituted polyethylenes, they are useful in accordance with preferred embodiments of the invention may be selected from polyacrylic acid, polymethacrylic acid, polyvinyl, tyrrolidone and polyvinyl alcohols.

One particularly advantageous family of gel forming polymers is in the family of acrylic acids and methacrylic acids, particularly when cross linked with divinyl glycols and particularly 3,4-dihyroxy-1,5-hexadiene, in view of several factors, including high water absorbing ability. One particularly preferred polymer in this family is polycarbophil, most preferably the acid form, and sold by B.F. Goodrich under the designation NOVEON AA-1. Polycarbophil is preferably present as at least 0.1, advantageously 0.1 to 2.0 and more preferably 0.3% to 0.7% of the gel formulation prior to any dehydration thereof.

The polysaccharides in accordance with preferred embodiments of the invention may be selected from cellulose or cellulose derivatives, (such as carboxymethylene, carboxymethylocellulose, and/or plasticized methyl or ethyl cellulose), glycoaminoglycans, agar, pectin, alginic acid, dextran, starch, and chitosan.

Starches occur in two forms, the alpha-amylose and amylopectin form. The more water soluble alpha-amylose form is preferred. Glycosaminoglycans in accordance with preferred embodiments of the invention can be selected from hyaluronic acid, chonocroitin, chondroitain-4-sulfate, chondroitin-6-sulfate, sematan sulfate, deratan sulfate, heparin sulfact ena heparin. Cycosaminoglycans and polysaccharides are advantageously included in formulations in accordance with preferred embodiments of the invention, in order to enhance the tissue conditioning and protection of the gum-line in expanded application use. Proteins are advantageously included in formulations in accordance with preferred embodiments of the invention, including collagen, gelatin and fibronectin. Advantageous acrylamide polymers include polyacrylamide or polymethacrylamide polymers. Biocompatible polyacrylamide polymers are preferred.

Gels in accordance with preferred embodiments of the invention can be lyophilized to provide a stable powder, from which gels can be reconstituted at the time of use, for use directly on dry sheets, foam or films, to deliver a dosage of the gel to the intended site of application, such as in the oral cavity. Also, powdered gels can be sprinkled under flaps of skin to hold the flap in place and promote healing.

Gels and composites employing the gels and the further processing thereof are useful in drop formulations, irrigating solutions, protective dressings, salves, as in liquid and solid form for wound healing and the like. A wound that may be healed using the compositions disclosed herein can be those which result from accidental or medical injury, surgically induced wounds, such as surgery in the oral cavity, such as those related to dental applications and cutaneous wounds, such as burn wounds, incision wounds, donor site wounds from skin transplants, ulcers (cutaneous, decubitis, venous stasis and diabetic). The gels and related embodiments thereof, such as films of the present invention may also be used for healing internal incisions as well as internal wounds, such as gastric ulcers.

In those applications where the gel, films or sheet are applied to an internal or incision wound, it is preferred that the gel, film, or foam forming polymer be degradable. Natural occurring polymers, such as collagen, glycoaminoglycans, gelatin and starch are generally degradable. Cellulose and cellulosics are generally not degradable. Synthetic polymers, such as vinyl polymers are not degradable.

Viscosity for gel formulation in accordance with preferred embodiments of the invention, prior to lyophilization of the composites is generally between 1,000 cps to 12,000,000 cps at room temperature (RT). A preferred viscosity ranges between 10,000 and 100,000 cps at RT.

Acrylamide polymers, particularly those exhibiting adhesive characteristics, may be useful in oral cavity applications. In one embodiment of the invention, the formulation can comprise 0.1% by weight acrylic polymer as a thickening agent and demonstrate a viscosity range between about 13,000 and 30,000 cps. In another embodiment of the invention, 0.5% acrylic polymer as thickener is used in the formulation demonstrate a viscosity range from 40,000 to 60,000 cps. In a more preferred embodiment, the acrylic polymer is comprised of polyacrylic acid cross linked with polyvinyl glycol and in a most preferred embodiment, comprises the acid form of polycarbophil. The polymer component can also be used to contain the "medicine" of the composition.

In another embodiment of the invention, the gel component may comprise 1–20% by weight cellulose derivative, having molecular weights from 5–700,000. In preferred embodiments, the cellulose derivative is present as 2–8% by weight and the preferred molecular weight range is from 50,000–300,000. Viscosities in the 10,000 to 200,000 cps range are also preferred. The preferred cellulose derivatives are hydroxypropyl cellulose (HPC), hydroxypropylmethyl cellulose (HPMC), methyl cellulose (MC), and carboxymethyl cellulose (CMC).

It will also be apparent to one of ordinary skill in the art that the desired viscosity range can be achieved by varying both the molecular weight and the percent concentration of the polymer in the formulation. For example, a gel having a relatively low viscosity can be formulated by using a low molecular weight polymer or a lower percent concentration of a higher molecular weight polymer, or a combination of the two. Thus, higher viscosity gels can be achieved by raising either the molecular weight of the polymer, the percent concentration of the polymer or both.

The gel, foam and/or film formulations in accordance with preferred embodiments of the invention can be used to coat fibers of an absorbent gauze dressing, nonporous, porous, or micro porous fabric as identified below and provide dressings that can be placed in the oral cavity. The gels, foams or film formulations of preferred embodiments of the invention can be applied to the dressing material by soaking, spray coating, dip coating or applying the material to the dressing material by mechanical means, such as the use of a doctor blade or other conventional coating methods.

The composite dressing can be processed, for example, through severe dehydration, by e.g., lymphilization and applied to the intended surface. The activity of the contained "medicine", in applications where such product is intended to deliver the "medicine" to an intended site, contacts the site to increase potential of intended activity.

The dressing material in accordance with preferred embodiments of the invention can include porous, non porous, or micro porous polyesters, rayons, cottons, wools, silks, papers, foams (open and closed cell), woven and non-woven fabrics, polyolefins, polyesters, copolyesters, polyurethanes, ethyl vinyl acetate, polyether block amides, ethylene methacrylic acids or polyethylenes. If applications in accordance with invention required potential ingestion of the product, degradable components should be used and should be of pharmaceutical or medical grade material, such as those designated by USP, NF, P, NF, etc. The biodegradability of various polymers are known to those in the art.

The biodegradability of the various polymers may also be related to the water solubility of the products that are produced from these raw materials. The degradability of the products produced can be directly related to the water solubility and effect of ions, such as salts, and other chemical aspects that may come in contact with the product once in the oral cavity or other site of intended application. A non-water soluble component of the product, addition of other raw materials to the formulation prior to, or following the freeze drying process may affect the solubility of the final product produced. The non-soluble component could be utilized to extend the time duration and treatment at the intended site of application. The non-soluble component could become, and be designed to dissolve after certain time exposure to application site fluids or enzymes, or release soluble items within the product itself or influenced by or a direct production of the application site utilized, such as bodily fluids.

Preferred embodiments of the invention will now be exemplified with reference to the following examples, which are presented for purposes of illustration only and are not intended to be construed as limiting.

EXAMPLE 1

A formulation was prepared, comprising 0.5% by weight Noveon AA-1;

0.5% by weight sorbic acid (preservative);

0.5% by weight sodium hydroxide; and 98.5% purified water.

A small portion, about 10% of the water was set aside and the remainder of the water was stirred to produce a type of vortex. Noveon AA-1 powder was slowly sifted into vortex and once addition was completed, the speed of mixing was reduced, in order to help avoid the introduction of air bubbles. The sorbic acid was then combined with half of the retained water and the sorbic acid solution was then mixed into the Noveon solution. The sodium hydroxide was mixed with the other half of the retained water and then slowly mixed into the solution. Once a uniform gel was produced, the product was poured off. It can be poured into a clear plastic pail and the top can be secured and sealed after filling.

EXAMPLE 2

To process the material into a freeze-dried foam, stainless steel trays were filled to 16.8 grams per $cm^2$ of the gel of Example 1. The trays were then inserted into pre-cooled freezer shelves of a freeze dryer at −45° C., with temperature monitoring probes inserted into the trays. After the tray contents reached a temperature of −40° C., the vacuum in the dryer was set to 100 mT (milli Torr) and the temperature was ramped slowly to 0° C. over the next six hours. The vacuum was maintained at 100 mT and the temperature was maintained at 0° C. for over ten hours. Then, with the vacuum maintained at 100 mT, the shelf temperature was ramped to 20° C. over the next four hours. The vacuum was then released and the product was removed and sealed from the room atmosphere.

At this point, the product can be cut to desired size in a controlled low moisture environment. Efforts should be made to minimize moisture exposure of the product to prevent re-hydration.

It is advantageous to place the dried foam-like product into a heat sealed "Tyzek" type pouch to seal the foam from the environment. If sterilized, the sealed product should be placed into a secondary pouch and sealed. In one preferred embodiment of the invention, sterilization is effected through gamma radiation exposure.

One particularly preferred use of dressings in accordance with the invention is to maintain whitening agents, such as various conventional buffered and unbuffered hydrogen peroxide and peroxide containing whitening agents against teeth. Tooth whitening agents, including various hydrogen peroxide derivatives and formulations which whiten teeth through peroxide activity are described in U.S. Pat. Nos. 3,657,413, 4,431,631, 4,537,413, 4,839,156 and 4,990,089, the contents of which are incorporated herein by reference.

Whitening agents can be applied to the gel, and one side of the gel can comprise a backing material such as an acrylic strip which will adhere to the gel, but will prevent adhesion to the oral surface behind the lips. Gels in accordance with the invention will conform to the irregular surfaces of the teeth when pressed in place. Thus, treatments of up to about 30 minutes or longer can be performed without the need for constructing a custom made tray to hold the whitening material to the teeth. Whitening strips can be pre-packaged, applied against the teeth and removed easily with or without water flushing.

It will thus be seen that the objects set forth above, among those made apparent from the preceding description, are efficiently obtained and, since certain changes may be made in carrying out the above method and in the articles set forth, without departing from the spirit and scope of the invention, it is intended that all matter contained in the above description shall be interpreted as illustrative and not in a limiting sense.

It is also to be understood that the following claims are intended to cover all of the generic and specific features of the invention herein described and all statements of the scope of the invention in which, as a matter of language, might be set to fall therebetween.

Particularly, it is to be understood that in said claims, ingredients or compounds recited in the singular are intended to include compatible mixtures of such ingredients, where ever the sense permits.

What is claimed is:

1. A method of treating a wound with a dressing material, comprising:
    forming a gel with a gel forming, amount of a water soluble or water swellable pharmaceutically acceptable polymer;
    dehydrating the gel to a preparation in the form a foam or powder form of the gel material;
    applying the preparation in either a rehydrated or non-rehydrated form to the wound site;
    the foam or powder in a suitable form, that it will adhere to a wound site for at least 24 hours and during that time, enhance healing of the wound and help prevent infection of the wound.

2. The method of claim 1, wherein the preparation is applied to a wound in the oral cavity.

3. The method of claim 1, wherein the polymer component comprises a member selected from the group consisting of polyoxyethylene—polyoxypropylene copolymers, polysaccharides, poly(ethylene oxide), acrylamide polymers, and salts and derivatives thereof.

4. The method of claim 1, wherein the polymer component comprises vinyl polymers or salts or derivatives thereof.

5. The method of claim 1, wherein the polymer component comprises salt or acid forms of polymers of acrylic or methacrylic acids crosslinked with divinyl glycol.

6. The method of claim 1, wherein the polymer component comprises the acid form of polycarbophil.

7. The method of claim 1, wherein the polymer component consists essentially of the acid form of polycarbophil.

8. The method of claim 1, wherein the gel is formed with at least about 0.1% by weight polycarbophil.

9. The method of claim 1, wherein the gel is formed with about 0.1 to 2.0% by weight polycarbophil.

10. The method of claim 1, wherein the gel is formed with about 0.3% to 0.7% by weight polycarbophil.

11. The method of claim 1, wherein the polymer component comprises at least one member selected from the group consisting of collagen, gelatin, fibronectin, cellulose, hydroxypropyl cellulose (HPC), hydroxypropylmethyl cellulose (HPMC), methyl cellulose (MC), ethyl cellulose (EC), carboxymethyl cellulose (CMC) and carboxyethyl cellulose (CEC).

12. The method of claim 1, wherein the gel is incorporated applied to a pharmaceutically acceptable carrier substrate prior to dehydration.

13. The method of claim 1, wherein the dehydrated gel is applied to a pharmaceutically acceptable carrier substrate after dehydration.

14. The method of claim 1, wherein the gel is dehydrated into the form of a powder and the wound comprises the area under a flap of tissue and the powder is applied to the wound and holds the flap in place.

15. The method of claim 1, comprising including an anti-bacterial agent in the dressing material.

16. A dressing for treating wounds, comprising the dehydrated form of a gel formed from a biocompatible polymer and water, said dehydrated gel being in the form of a foam sheet or a powder that will adhere to tissue at a wound site, promote healing of a wound covered by the dressing and help protect the wound from infection.

17. A wound dressing comprising the acid form of polycarbophil in the form of a gel, foam or powder.

18. A method of treating a wound, comprising:
    applying the dehydrated powder or foam form of an aqueous based gel of a polymer comprising polycarbophil to the wound.

19. The method of claim 18, wherein the wound is in the oral cavity.

20. The method of claim 18, wherein the wound comprises a flap of tissue, comprising applying the powder form of a dehydrated gel under the fly of tissue to hold down the flap, help prevent infection and increase the rate of healing of the wound.

21. A tooth whitener, comprising a layer of polycarbophil having tooth whitening material combined therewith.

22. The tooth whitener of claim 21, wherein the tooth whitening material comprises buffered or unbuffered hydrogen peroxide.

23. The tooth whitener of claim 22, wherein one side of the layer of gel is backed with material which will not adhere to the teeth or gums.

24. The tooth whitener of claim 21, wherein the layer of polycarbophil comprises dehydrated polycarbophil gel.

25. A method of whitening teeth, comprising forming a gel with a gel forming amount of a water soluble or water swellable pharmaceutically acceptable polymer; dehydrating the gel and forming a sheet of dehydrated gel material; combining the gel with tooth whitening material before of after the gel is dehydrated; and adhering the layer of gel with tooth whitener to the teeth.

26. The method of claim 25, wherein the tooth whitener is added after the layer is formed.

27. The method of claim 25, wherein the tooth whitener is added before the layer is formed.

28. The method of claim 25, wherein the gel comprises polycarbophil.

29. The method of claim 25, wherein the tooth whitener comprises hydrogen peroxide.

30. The method of claim 25, wherein the tooth whitener comprises a peroxide containing material.

\* \* \* \* \*